US00PP08060P

United States Patent [19]

Collicutt

[11] Patent Number: Plant 8,060

[45] Date of Patent: Dec. 15, 1992

[54] ROSE PLANT — MORDEN FIREGLOW VARIETY

[75] Inventor: Lynn M. Collicutt, Morden, Canada

[73] Assignee: Her Majesty the Queen in right of Canada, as represented by the Minister of Agriculture, Ottawa, Canada

[21] Appl. No.: 680,695

[22] Filed: Apr. 4, 1991

[51] Int. Cl.[5] ..... A01H 5/00
[52] U.S. Cl. ..... Plt./1
[58] Field of Search ..... Plt. 1, 28, 29

*Primary Examiner*—Howard J. Locker
*Attorney, Agent, or Firm*—Burns, Doane, Swecker & Mathis

[57] ABSTRACT

A new and distinct variety of shrub rose plant is provided which forms attractive relatively large semi-double red blossoms having reflexed sepals. The variety exhibits an erect growth habit, exhibits good winter hardiness, and commonly assumes a height of approximately one meter. The new variety propagates well by the use of softwood stem cuttings, and is well adapted for growing as colorful ornamentation in the landscape.

4 Drawing Sheets

SUMMARY OF THE INVENTION

The new variety of shrub rose plant of the present invention was created by artificial pollination at the Morden Research Station Morden, Manitoba, Canada. The new variety is a complex hybrid that was developed from *Rose arkansana* Porter, the *R. arkansana* hybrids, ASSINIBOINE and MORDEN AMORETTE, the floribunda, WHITE BOUQUET (U.S. Plant Pat. No. 1,415), PRAIRIE PRINCESS and MORDEN CARDINETTE. PRAIRIE PRINCESS is listed as a shrub rose and has *R. laxa* Retz. and *R. spinosissiama* L. in its parentage. Accordingly, the new variety has three hardy species in its background. The parentage of the new variety can be summarized as follows:

Seed parent — [{{(*Rosa arkansana*×ASSINIBOINE)×WHITE BOUQUET}×PRAIRIE PRINCESS}×MORDEN AMORETTE].
Pollen parent — [MORDEN CARDINETTE].

Selective study resulted in the identification of a single plant of the new variety.

It was found that the new variety of shrub rose plant of the present invention possesses the following combination of characteristics:

(a) forms attractive relatively large semi-double red blossoms having reflexed sepals,
(b) exhibits an erect growth habit,
(c) exhibits an aptitude for propagation by the use of softwood stem cuttings,
(d) exhibits good winter hardiness, and
(e) is particularly well suited for growing in the landscape.

The new variety well meets the needs of the horticultural industry. It can be grown to advantage as attractive ornamentation in parks, gardens, public areas, and residential landscapes. It is particularly well suited for growing in the landscape.

The characteristics of the new variety have been found to be homogeneous and stable and are strictly transmissible by asexual propagation (such as softwood stem cuttings) conducted at Morden, Manitoba, Canada, from one generation to another.

The new variety has been named the MORDEN FIREGLOW variety.

BRIEF DESCRIPTION OF THE PHOTOGRAPHS

The accompanying photographs show, as nearly true as it is reasonably possible to make the same in color illustrations of this character, typical specimens of plant parts of the new variety. The rose plants of the new variety described herein were grown outdoors at Morden, Manitoba, Canada.

FIG. 1 — illustrates an open red blossom and typical foliage of the new variety;

FIG. 2 — illustrates specimens of leaves having five and three leaflets — plan view — obverse;

FIG. 3 — illustrates specimens of leaves having five and three leaflets — plan view — reverse;

FIG. 4 — illustrates on the left a floral receptacle showing the arrangement of the stamens (sepals removed), and on the right a floral receptacle showing the arrangement of the pistils (sepals and stamens removed);

FIG. 5 — illustrates a specimen of new growth;

FIG. 6 — illustrates when viewed from left to right a floral sequence which shows the opening of a bud during blossom formation and the typical disposition of the sepals, as well as a hip at the far right;

FIG. 7 — illustrates an open flower — plan view — obverse;

FIG. 8 — illustrates an open flower — plan view — reverse wherein the reflexed sepals also are visible; and FIG. 9 — illustrates a representative floral petal showing a typical vein pattern.

DETAILED DESCRIPTION

Figure 1:
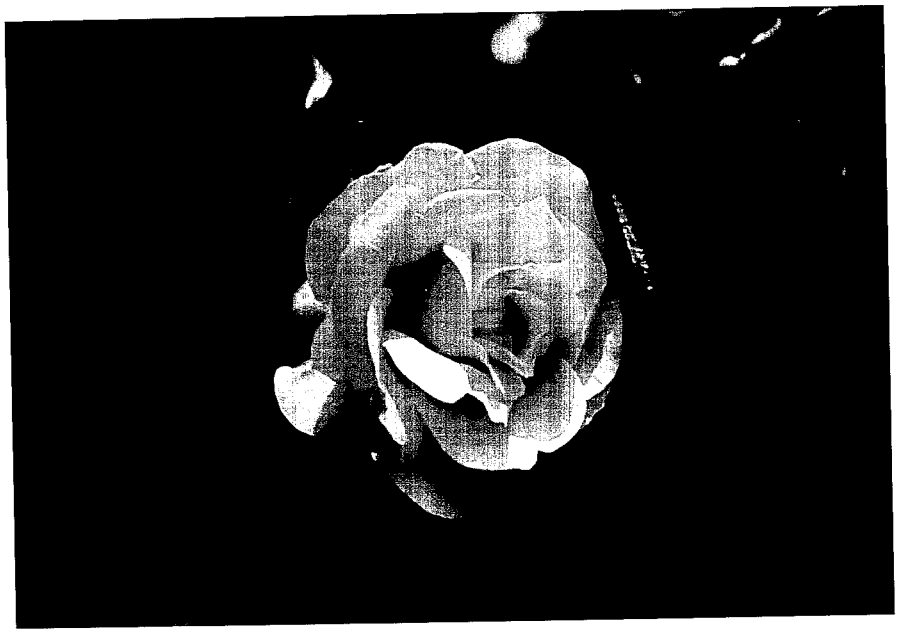
Figure 2:
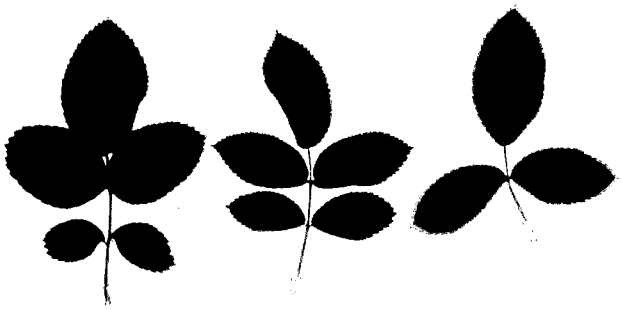
Figure 3:
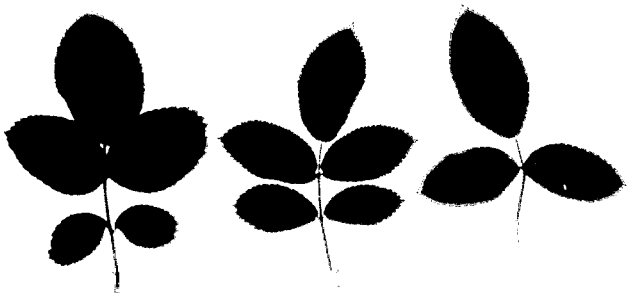
Figure 4:
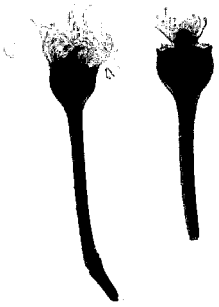
Figure 5:
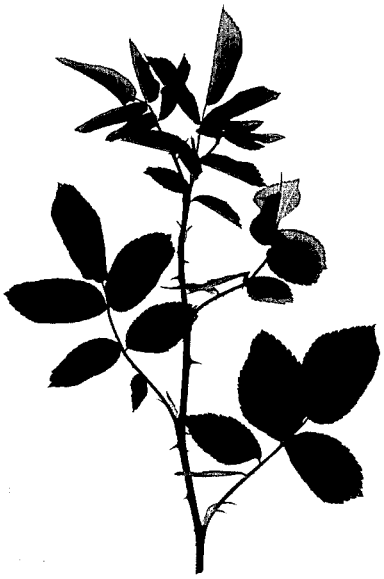
Figure 6:
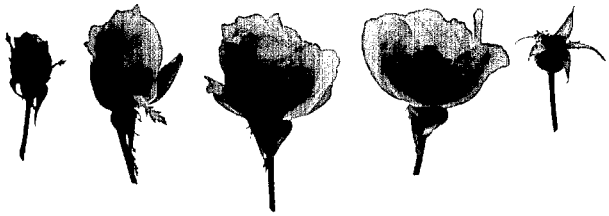
Figure 7:
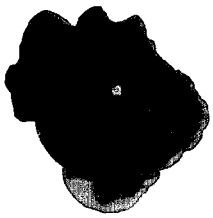
Figure 8:
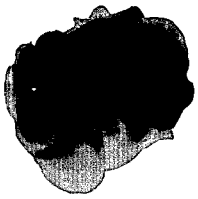
Figure 9:
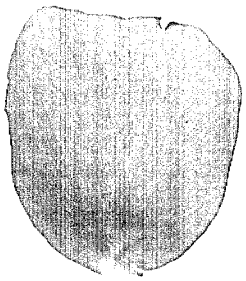

The chart used in the identification of colors is that of The Royal Horticultural Society (R.H.S. Colour Chart). Common color terms are to be accorded their ordinary dictionary significance. The description is based on the observation of specimens of the new variety while grown outdoors at Morden, Manitoba, Canada.

Class: Shrub.
Plant:

*Height.*—Approximately 1 meter.

*Width.*—Approximately 65 cm. on average.

*Habit.*—Erect.

Branches:

*Color.*—Young stems: bronze green, Yellow-Green Group 146B to 146C, and slightly shaded with reddish coloration during cooler growing conditions. Mature stems: bronze green, Yellow-Green Group 146B to 146C, and slightly shaded with reddish coloration during cooler growing conditions.

*Prickles.*—Shape: concave on upper edge, deeply concave on under edge, and the base is dilated. Size: small to medium. Quantity: moderately numerous. Color: yellow-green with a reddish base or red on young stems.

Leaves: Compound and pinnate.

*Stipules.*—Adnate, fairly narrow and linear, hairs along edge to slightly glandular, auricles are erect.

*Petioles.*—Upper surface: grooved green in coloration, and slightly glandular. Under surface: green with a few small hooked prickles.

*Petiolules.*—Very short or non-existent.

*Foliage.*—Number: 3, 5 or 7. Shape: oval to rounded base, acute tip, with hairs along veins on underside. Serration: single and fairly regular. General appearance: semi-dull. Color (young foliage): upper surface: medium green, Yellow-Green Group 147A to 147B. under surface: medium green, Yellow-Green Group 147B. Color (adult foliage): upper surface: Yellow-Green Group 146A to 146B. under surface: Yellow-Green Group 146B.

Inflorescence:

*Number of flowers.*—Usually 1 to 9 per stem.

*Peduncle.*—Erect, rigid, light green, and slightly glandular.

*Sepals.*—Upper surface: tomentose, greenish in coloration, may also bear a slightly reddish coloration. Under surface: light green in coloration, very slightly glandular. The outer sepals have slightly glandular edges and bear a few appendages.

*Buds.*—Shape: pointed before opening of the sepals. Length: approximately 2.5 cm. on average outside the calyx at the opening of the sepals. Size: medium. Color upon opening: upper surface: Red Group 43B. under surface: Red Group 50A.

*Flower.*—Shape: initially globular, and subsequently changing in form to a hollow cup, semi-double flower, center petals tend to infold and to loosely cover the stigmas. Diameter: approximately 6 to 8 cm. on average. Color (when opening begins): upper surface: Red Group 43A to Red Group 44A. Color (when blooming): upper surface: Red Group 43A to Red Group 44A. under surface: Red Group 45A to 45C, as well as Red Group 46B. Color (at end of blooming): Red Group 44C to Red Group 45B and 45C with spots and streaks of Red Group 46B. Fragrance: slight. Petal form: broad elliptic to circular in shape. Petal texture: intermediate. Petal number: approximately 28 on average. Petal drop: the petals drop off cleanly. Anthers: light yellow changing to gold in coloration: Filaments: cream to light yellow in coloration and changing to a somewhat reddish coloration where anthers attach. Stigmas: light yellow in coloration. Styles: hairy along length, reddish in coloration at top, located below the anthers, and not attached to each other. Receptacle: light green at the dehiscence of the anthers, in longitudinal section it is globular and in the shape of a cup, and forms fertile hips with the sepals often being retained in a somewhat reflexed configuration often in the absence of dehiscence; however, sometimes a few sepals will dihisce.

Development:

*Vegetation.*—Intermediate vigor.

*Blossoming.*—Intermediate.

*Hardiness.*—Good.

*Resistance to diseases.*—Moderate.

*Preferred mode of propagation.*—Softwood stem cuttings.

I claim:

1. A new and distinct variety of shrub rose plant characterized by the following combination of characteristics:

(a) forms attractive relatively large semi-double red blossoms having reflexed sepals,
(b) exhibits an erect growth habit,
(c) exhibits an aptitude for propagation by the use of softwood stem cuttings,
(d) exhibits good winter hardiness, and
(e) is particularly well suited for growing in the landscape;

substantially as herein shown and described.

* * * * *